United States Patent [19]

Kerkhof et al.

[11] 4,264,581
[45] Apr. 28, 1981

[54] SUNSCREEN COMPOSITION

[75] Inventors: Nicholas J. Kerkhof, Los Altos, Calif.; Anne M. Herrold, Brownsburg, Ind.

[73] Assignee: Eli Lilly and Company, Indianapolis, Ind.

[21] Appl. No.: 54,375

[22] Filed: Jul. 2, 1979

[51] Int. Cl.³ .......................... A61K 7/42; A61K 7/44
[52] U.S. Cl. ........................................ 424/60; 424/59; 424/357; 424/365
[58] Field of Search ..................................... 424/59, 60

[56] References Cited

FOREIGN PATENT DOCUMENTS 2706782 9/1977 Fed. Rep. of Germany ............. 424/60
1305872 8/1962 France ....................................... 424/59
47-42500 10/1972 Japan ......................................... 424/59

OTHER PUBLICATIONS

Sayre et al., Photochem. & Photobiol., 1979, vol. 29, pp. 559 to 566.
Sayre et al., Arch. Derm., 1/1979, vol. 115, pp. 46 to 49.
Markland, Cosm. & Toiletries, 3/1976, vol. 91, pp. 79 to 81.

*Primary Examiner*—Dale R. Ore
*Attorney, Agent, or Firm*—Karen B. O'Connor; Arthur R. Whale

[57] ABSTRACT

An improved sunscreen composition containing the active ingredients 2-ethylhexyl-N,N-dimethyl-p-aminobenzoic acid and 2-hydroxy-4-methoxybenzophenone is described.

3 Claims, No Drawings

SUNSCREEN COMPOSITION

This invention relates to a novel sunscreen composition which, when applied to human skin provides improved protection against erythema (redness) caused by ultraviolet radiation from sunlight.

Sunscreen compositions are commonly used during outdoor work or leisure for protection of exposed skin against painful sunburn. Many effective sunscreen preparations are sold commercially or are described in the cosmetic or pharmaceutical literature. In general, sunscreen preparations are formulated in the form of a cream, lotion or oil containing as the active agent an ultraviolet radiation absorbing chemical compound. The active agent acts to block the passage of erythematogenic radiation thereby preventing its penetration into the skin.

The ideal sunscreen formulation should be non-toxic and non-irritating to skin tissue and be capable of convenient application to the skin in a uniform continuous film. The product should be sufficiently stable chemically and physically so as to provide an acceptable shelf life upon storage. It is particularly desirable that the preparation should retain its protective effect over a prolonged period after application. Thus, the active agent when present on the skin must be resistant to chemical or photodegradation, to absorption through the skin, and to removal by perspiration, skin oil, or water. For esthetic reasons, the product should be substantially odorless (or be capable of being scented) and be non-staining to the skin or clothing.

Two agents known to be effective sunscreen agents are 2-ethylhexyl-N,N-dimethyl-p-aminobenzoate (also known as octyl dimethyl, p-aminobenzoic acid ester), and 2-hydroxy-4-methoxy benzophenone (also known as oxybenzone). Each of these compounds has been employed alone, or in combination, in various sunscreen preparations. [see, for example, R. N. Sayre et al., *Photochemistry and Photobiology*, 29, 559 (1979) and *Arch. Dermatol.*, 115, 46 (1979)]. It has been surprisingly found that a novel sunscreen composition employing the aforesaid chemical agents provides a superior sun protection factor (SPF) when evaluated in human subjects in standard solar simulator tests. Moreover, the novel composition affords superior resistance to removal of the active agents from the skin by water, as evidenced in standard whirlpool wash-off tests.

In accordance with this invention there is provided a sunscreen composition substantially having the following formulation, by weight:

| | |
|---|---|
| 2-ethylhexyl-N,N-dimethyl-p-aminobenzoate | 8% |
| 2-hydroxy-4-methoxy-benzophenone | 3% |
| polyethylene having a molecular weight of about 1500 | 4% |
| mineral oil | 8% |
| triglycerol di-isostearate | 5.5% |
| beeswax | 4% |
| organically modified montmorillonite clay gellant | 1.5% |
| isopropyl myristate | 13.5% |
| sorbitol, as 70% aqueous solution | 7.5% |
| water | q.s. |

It will be apparent to those skilled in the art that a small effective amount of a conventional preservative, coloring agent or fragrance (essence) can be added if desired to the afore-described formulation, and the compositions containing such added substances are also within the scope of the present invention. The term "small effective amount" means an amount of the added ingredient sufficient to impart the desired effect, but the amount must not adversely affect the physical or chemical stability or effectiveness of the composition in which it is utilized. For example, in order to improve the shelf-life of the product, up to about 1% of a preservative (or a mixture thereof) can be included. Suitable preservatives are the alkyl parabens (e.g. a methyl, ethyl, propyl, benzyl or butylparaben), imidazolidinyl urea, cis-1-(3-chloroallyl)-3,5,7-traza-1-azonia-adamantane chloride (Dowacil ® 200, Dow Chemical Co.) and potassium sorbate. For esthetic purposes, up to about 1% of a fragrance or coloring agent can be added. The use of preservatives, fragrances, and coloring agents in sunscreen preparations is well known in the art, and the selection of a particular added substance, and its amount, will be readily apparent. The preservative, coloring agent, or fragrance must be non-toxic and non-irritating to the skin in the amounts employed.

The aforesaid formulations may also include optionally an acceptable, compatible base in an amount sufficient to neutralize the free fatty acids present in the beeswax component. The use of such a base is preferred since it improves the quality of the emulsion. Up to about 0.5% of the base may be added. Suitable bases are sodium tetraborate, sodium hydroxide, potassium hydroxide, and the like, although other bases will be recognized by those skilled in the art. The base must be non-toxic and non-irritating to the skin in the amounts employed.

In general, the individual components used in the formulation should be of a quality or purity (such as U.S.P. or N.F.) suitable for cosmetic use.

The polyethylene employed in the compositions is a homopolymer having an average molecular weight of about 1500. A polyethylene homopolymer acceptable for use in the compositions of the present invention is available from Allied Chemical Company, Morristown, New Jersey under the name "A-C ® Polyethylene 617." This polyethylene exhibits the following characteristics:

Softening point (ASTM E-28): 102° C.
Hardness (ASTM D-5): 8 dmm
Viscosity (Brookfield), 140° C.: 180
Density (ASTM D-1505): 0.91 g/cc An organically modified montmorillonite clay gellant is available from NL Industries, Hightstown, New Jersey, under the name "Bentone ® 38" and this substance is preferred. The aforesaid clay is also available under the name "Bentone Gel IPM" which is composed of a mixture of modified montmorillonite clay and isopropyl myristate. This mixture can be used as a source of both the clay gellant and isopropyl myristate, if desired.

The sunscreen compositions of this invention are prepared by mixing the ingredients according to conventional methods. It is important that the final bulk product at 40°–45° C. be subjected to high sheer by passage through a colloid mill or homogenizer. The following illustrates a preferred formulation and its method of preparation:

A. Formulation:

| Ingredient | % by weight |
|---|---|
| fragrance | 0.300 |
| triglycerol diisostearate | 5.500 |
| sodium tetraborate | 0.380 |
| mineral oil, light | 8.000 |
| organically modified montmorillonite clay gellant (Bentone ® 38) | 1.500 |
| beeswax, white | 4.000 |
| methylparaben | 0.200 |
| propylparaben | 0.200 |
| isopropyl myristate | 13.500 |
| sorbitol solution, 70% | 7.500 |
| imidazolidinyl urea | 0.400 |
| 2-ethylhexyl-N,N-dimethyl-p-aminobenzoate | 8.000 |
| 2-hydroxy-4-methoxybenzophenone | 3.000 |
| polyethylene (A-C ® Polyethylene 617) | 4.00 |
| Water, deionized | 43.52 |
| Total | 100.000 |

Procedure:

Phase A: Mineral oil and A-C® Polyethylene 617 are mixed at 90°-95° C. with a high speed stirrer (Lightnin') until a clear solution is formed. The phase is maintained at 90°-95° C. under moderate agitation until needed.

Phase B: A mixture of beeswax; Bentone ® 38; triglycerol diisostearate; isopropyl myristate; propylparaben; 2-ethylhexyl-N,N-dimethyl-p-aminobenzoate, and 2-hydroxy-4-methoxybenzophenone is heated at 90°-95° C. with moderate agitation until the phase is uniform. The phase is maintained at 90°-95° C. with moderate agitation until needed.

Phase C: The following ingredients are mixed at 90°-95° C. with moderate agitation: deionized water (5% excess), sorbitol solution (70% aqueous), methylparaben, sodium tetraborate, and imidazolidinyl urea. Mixing is continued until all materials are dissolved. The phase is maintained at 90°-95° C. with moderate agitation until needed.

Mixing of Phases A, B, C: Phase A is added to phase B and the resulting mixture (Phase AB) is stirred until uniform. The phase is maintained at 90°-95° C. with moderate agitation. Phase C is added to Phase AB, and the resulting mixture is stirred at 90°-95° C. The product is passed through a colloid mill with a ⅜ closed setting (Fryma ® set at 0.7 mm) and the product is circulated until homogeneous. The product is removed and cooled to 40°-45° C. The fragrance is then added to the cooled product and mixing is continued until the product is uniform. With temperature maintained at 40°-45° C. the scented bulk product is then passed through the colloid mill with a ⅜ closed setting and discharged into a storage container.

What is claimed is:

1. A sunscreen composition consisting essentially of the formulation:

| | |
|---|---|
| 2-ethylhexyl-N,N-dimethyl-p-aminobenzoate | 8% |
| 2-hydroxy-4-methoxybenzophenone | 3% |
| polyethylene having a molecule weight of about 1500 | 4% |
| mineral oil | 8% |
| triglycerol di-isostearate | 5.5% |
| beeswax | 4% |
| organically modified montmorillonite clay gellant | 1.5% |
| isopropyl myristate | 13.5% |
| sorbitol, as 70% aqueous solution | 7.5% |
| water | q.s. |

2. A sunscreen composition having substantially the formulation defined in claim 1 which further includes therein an effective amount of a non-toxic and non-irritating preservative, fragrance, coloring agent, or a compatible base, said base being capable of neutralizing the free fatty acids present in the beeswax component.

3. A sunscreen composition having substantially the formulation defined in claim 1 which further includes therein methylparaben, 0.200%; propylparaben, 0.200%; imidazolidinyl urea, 0.4%; sodium tetraborate, 0.380%; and a fragrance, 0.300%.

* * * * *